United States Patent [19]

Chang

[11] 4,101,673

[45] Jul. 18, 1978

[54] PURIFICATION OF NUTRITIVE OILS

[75] Inventor: Stephen S. Chang, East Brunswick, N.J.

[73] Assignee: Vitrum AB, Stockholm, Sweden

[21] Appl. No.: 745,069

[22] Filed: Dec. 13, 1976

Related U.S. Application Data

[63] Continuation-in-part of Ser. No. 498,568, Aug. 19, 1974, abandoned.

[51] Int. Cl.$^2$ ............................................. A01N 9/24
[52] U.S. Cl. .................................................... 424/312
[58] Field of Search ........................................ 424/312

[56] References Cited

U.S. PATENT DOCUMENTS

| | | | |
|---|---|---|---|
| 2,819,199 | 1/1958 | Kalish | 424/312 |
| 2,945,869 | 7/1960 | Meyer et al. | 424/312 |
| 2,972,565 | 2/1961 | Zilversmit | 424/312 |
| 2,977,283 | 3/1961 | Meyer et al. | 424/312 |
| 3,169,094 | 2/1965 | Wretlind | 424/312 |
| 3,754,086 | 8/1973 | Fujisawa | 424/241 |
| 3,798,246 | 3/1974 | Shimazaki et al. | 260/403 |

FOREIGN PATENT DOCUMENTS

| | | |
|---|---|---|
| 1,592,582 | 6/1970 | France. |
| 79,916 | 2/1971 | German Democratic Rep. |
| 828,312 | 2/1960 | United Kingdom. |

OTHER PUBLICATIONS

Singleton et al., J. Am. Oil Chem. Soc. (1966), 43(10), pp. 592–595.
Jensen et al., Lipids 1(6), pp. 451–452 (1966).
Min et al., J. Am. Oil Chem. Soc. (1972) 49(12) 675–677.
Lin – Thesis 10/1968, Rutger's Univ.

Primary Examiner—Albert T. Meyers
Assistant Examiner—D. W. Robinson
Attorney, Agent, or Firm—Cook, Wetzel & Egan, Ltd.

[57] ABSTRACT

Parenterally administrable oil-in-water emulsions formed from nutritive oils, such as soybean and sunflower oils, are improved first by treating the nutritive oil with silicic acid to remove undesirable components such as peroxides, pigments, thermal and oxidative decomposition products, certain unsaponifiable matter such as sterols, and polymers. Purification is effected by treating the oil with silicic acid or silica gel either directly, or as a solution thereof in a suitable solvent, such as hexane. Autoxidation of the purified oil is prevented by adding to the purified oil a tocopherol antioxidant, $\gamma$-tocopherol being preferred. There is also added a metal scavenging agent such as ascorbyl palmitate.

7 Claims, 4 Drawing Figures

PURIFICATION OF NUTRITIVE OILS

This application is a continuation-in-part of my copending application Ser. No. 498,568, filed Aug. 19, 1974 (now abandoned).

BACKGROUND OF THE INVENTION

1. Field of the Invention

This invention relates to a nutritive oil in water emulsion for use in parenteral administration, wherein said nutritive oil is refined or purified soybean oil or sunflower oil. The invention further relates to the purification of nutritive oils used in oil in water emulsions for parenteral feeding, such as soybean and sunflower oil, and in particular, the invention relates to the removal from such oils of undesirable components such as peroxides, pigments and thermal and oxidative decomposition products and polymers. Autoxidation of the purified oil is prevented by adding to the purified oil a tocopherol antioxidant, preferably γ-tocopherol, along with a metal scavenging agent such as ascorbyl palmitate.

2. The Prior Art

Glucose in solution has long been used for the purpose of parenteral nutrition. However, emulsions of certain nutritive oils in water have certain definite advantages over glucose solutions for that purpose. Firstly, oil has a higher caloric content than does glucose. Secondly, since oil is insoluble in water, it does not exert an osmotic effect and thus, can be used in vivo at higher concentrations than can glucose. However, when oil in water emulsions are used for intravenous feeding, there are several distinct problems which must be contended with. Thus, such oil in water emulsions, when injected intravenously, can cause many adverse physiological effects, such as back pain, fever, chills, headache, dizziness, blood pressure fluctuations, liver damage, and the so-called "overloading syndrome", and also, the emulsion may be damaged during storage and transportation under refrigerated temperatures.

A commercial prior art oil-in-water emulsion sold under the name Intralipid is understood to be produced in accordance with the teachings of U.S. Pat. No. 3,169,094 to Wretlind. The literature has reported that abnormalities have been observed in liver function tests during hyperalimentation with Intralipid. Significant eosinophilia has been reported, as well as elevated alkaline phosphatase and brown pigmentation of the reticuloedothelial system of the liver. Swelling of both the mitochondria and endoplasmic reticulum have been noted. Febrile responses, chills, sensation of warmth, shivering, vomiting and pain in chest and back, thrombophelbitis have been observed. [See: A. G. Coran, The Hyperalimination of Infants with a Commercial Fat Emulsion, 110-117. Proceedings of a meeting on Intravenous Feeding held in Vancouver, Canada, January, 1974; Margaret R. Pendray, Peripheral Vein Feeding in Infants: Techniques, Results and Problems, 158-176. Proceedings of a meeting on Intravenous Feeding held in Vancouver, Canada, January, 1974; and Hallberg et al. Fat Emulsion for Complete Intravenous Nutrition. Postgrad. Med. 1967, 42, A-71, 87, 99, 149.]

It is an object of this invention to provide a process for purifying such nutritive oils to remove from the oils those substances which are at least partly responsible for the problems associated with their use in parenteral emulsions. Among these substances are peroxides, pigments, unsaponifiables such as sterols, and thermal and oxidative decomposition products and polymers. It is a further object of the invention to provide a process whereby autoxidation of the purified oils may be retarded.

It has been demonstrated that oils which have been subjected to elevated temperatures in the presence of oxygen from oxidative decomposition products and polymers and that such oxidized oils are toxic. It has been reported that certain fractions of such oxidized oils, and particularly certain of the non-urea-adduct-forming ester fractions are highly toxic when substituted for fresh fats in the diets of test animals. Generally it has been found that the non-urea-adduct-forming materials found in oxidized oils showed a high deviation of organ size (organ enlargement and liver growth depression similar to the liver damage observed in testing Intralipid) in test animals as well as irritation of the digestive tract, cancer and death. [See: Acute Physiological Effects of Feeding Rats. Non-urea-adducting Fatty Acids. Shue, G. M., Douglass, D. C., and Firestone, D. Jour. Nutrition 94, 171-178 (1968); The Effect of Heated Fat on the Carcinogenic Activity of 2-Acetylaminofluorene. Sugai, M., Witting, L. A., Tsuchiyama, H., and Kummerow, F. A. Cancer Res. 22, 510-19 (1962); and The Chemical and Biological Properties of Heated and Oxidized Fats. Artman, N. R. Advances in Lipid Research 7, 245-330 (1969).]

Many techniques have been proposed in the prior art for purifying nutritive oils for use in oil in water emulsions for parenteral feeding, but none of these techniques involves the use of silicic acid for removing the above-described impurities. [See, e.g., Singleton et al, "A Method For Adsorbent Fractionation of Cottonseed Oil For Experimental Intravenous Fat Emulsions", The Journal of the American Oil Chemists' Society, Vol. 43, pp. 592-595 (1966), which describes, in connection with the preparation of aqueous cottonseed emulsions for parenteral administration, removal of pigments and polar components of cottonseed oil by sequentially treating the oil with bleaching earth and alumina adsorbents.] Similarly U.S. Pat. No. 3,169,094 to Wretlind, describes mild extraction of soybean oil with an organic solvent such as ethanol, ether, or petroleum ether, and deodorization with active carbon and alumina, followed by preparing an aqueous emulsion of the thus treated soybean oil and egg phosphatides, this emulsion being suitable for parenteral administration. As was mentioned above, the commercial version of oil-in-water emulsions produced in accordance with the Wretlind teaching has not been free from problems.

Further, the literature reports that alumina causes decomposition of lipids, and that the treatment of oil with alumina is likely to form various undesirable decomposition products. [See, e.g., "Lipid Chromatographic Analysis", Edited by Guido V. Marinetti, Vol. 1, published by Marcel Dekker, Inc., New York, 1967, page 221, which states:

"Bertstrom (103) and others found, however, that alumina caused alterations in lipid structure during chromatography, namely, alumina partially hydrolyzed glycerides and other fatty acid esters, isomerized mono- and diglycerides, promoted autoxidation and isomerization of double bonds, and caused dehydration of peroxidized lipids."

"Autoxidation of Linoleic Acid" by D. Le Mammick and S. F. Mason, Nature, 156, 717-718 (1945), report the dehydration of peroxides of linoleic acid (a major component of soybean oil and sunflower oil) on treatment with alumina; and "Artifacts Found During Alumina Chromatography", by B. M. Lawrence, J. W. Hogg and S. J. Terhune, Journal of Chromatography 12, 261-262 (1960), reported the dimerization and trimerization of vegetable oil components which were chromatographed with alumina.]

SUMMARY OF THE INVENTION

According to one aspect of the present invention, there is provided an aqueous emulsion of refined or purified soybean oil or of sunflower oil, which emulsion is highly advantageous for parenteral administration.

According to another aspect of the invention, there is provided a method of purifying nutritive oils to remove therefrom impurities such as peroxides, pigments, unsaponifiables such as sterols, and thermal and oxidative decomposition products and polymers by passing the oil through a column or a layer of a suitable siliceous adsorbent, such as silicic acid or silica gel. The treatment of nutritive oils by the method of the present invention removes therefrom a group of impurities generally known as "non-urea-adduct-forming esters". The impurities removed from nutritive oils by the process of the present invention are chemically similar to the non-urea-adduct-forming esters found in thermally oxidized vegetable oils, as shown by infrared and NMR-spectraphotometry. It has been demonstrated that when a soybean oil is treated in accordance with the teachings of Example 1 of U.S. Pat. No. 3,169,409 to Wretlind, that the product is highly colored and has a strong odor. When such an oil is passed through a silicic acid column, in accordance with the present invention, a light colored oil is obtained. The impurities which remain in the column as a color band and which can be recovered from the column, have been shown by infrared and NMR-spectraphotometry to be chemically similar to the impurities removed from commercially refined soybean oil using the present invention.

As was mentioned above, it has been reported that such impurities, and particularly the non-urea-adduct-forming esters found in thermally oxidized oils are markedly toxic when substituted for fresh oils in the diets of test animals. Thus the present invention contemplates the removal of potentially toxic materials from nutritive oils and that the resulting purified oil is adapted to produce an improved oil-in-water emulsion for use in parenteral nutrition. In addition to producing an oil having a reduced level of impurities, it has been discovered that silicic acid also has a higher capacity to treat oil, as is reported in Table IV below. Such increased capacity results in a more economical process and a lower cost, improved product.

The oil which has been purified in accordance with the present invention, while having considerably less of the above-mentioned impurities than does the original oil, may undergo autoxidation at a faster rate, with the possibility of forming more undesirable peroxides. In order to stabilize the thus purified oil and retard its tendency toward undergoing autoxidation, the invention further provides a method for stabilizing the purified oil which involves adding to the purified oil a tocopherol antioxidant, preferably γ-tocopherol, desirably together with a scavenging agent such as ascorbyl palmitate, to thereby increase its resistance toward autoxidation. As a result of this stabilization, emulsions prepared from the purified and stabilized oil may be stored and transported without undergoing an excessive degree of oxidative decomposition.

DETAILED DESCRIPTION OF THE INVENTION

Figure 1:
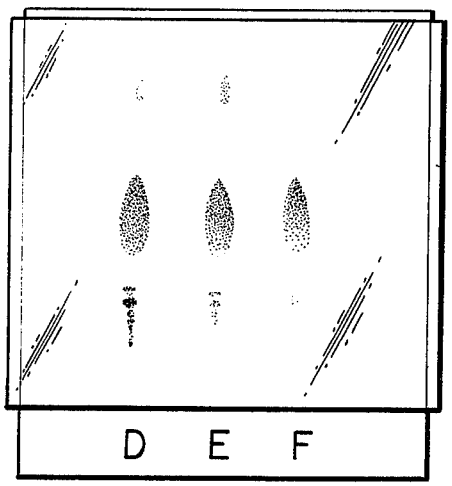
FIG. 1 is a photograph of a silicic acid thin layer chromatogram of a soybean oil sample before and after purification on a silicic acid column.

There will now be given a detailed description of the invention, which description will be best understood when taken in conjunction with the accompanying drawings.

I. PURIFICATION OF OILS BY SILICIC ACID COLUMN CHROMATOGRAPHY

1. Soybean Oil

Silicic acid of 100 mesh particle size, such as the Analytical Reagent Grade manufactured by Mallinckrodt Chem. Works, was washed and activated according to the method described by Sahasrabudhe et al in Jour. Amer. Oil Chem. Soc. 38:88, 1961. Three hundred gm of the washed, activated silicic acid were used to pack a chromatographic column of 40 mm. diameter to an approximate height of 50 cm. A commercially refined, bleached and deodorized soybean oil was passed through the column by either applying vacuum at the bottom or pressure at the top, or both. The temperature of the column was maintained at room temperature throughout the procedure. If desired, the column may be wrapped with an electric heating tape to increase its temperature to about 60°-80° C, which has the effect of significantly increasing the flow rate of the oil through the column. The oil can be passed through the column alone or in the form of a solution in a solvent, such as hexane. To prevent oxidation of the oil, the process may be conducted under an inert atmosphere such as nitrogen. When the oil or a solution thereof was passed through the column, the impurities in the oil which included peroxides, pigments, unsaponifiables, polar monomers, and thermal and oxidative decomposition products and polymers were adsorbed on the column as a dark colored band. The first 25 gm. or so of eluate were collected separately for later analysis. The oil or solution thereof was continuously fed into the column until the colored band moved down the column. The passage of oil through the column was continued until the dark colored band approached the bottom of the column. The eluate or purified oil, after passing through the silicic acid column was suitable for the preparation of oil in water emulsions for parenteral feeding.

The soybean oil, both before and after passage through the silicic acid column was analyzed for color by Official Method Cc-13c-50 of the American Oil Chemists' Society, unsaponifiable matter by Official Method Ca-6a-40 of the American Oil Chemists' Society, and non-urea-adduct-forming esters by the method of Firestone described in Journal of the American Oil Chemists' Society 38, 418–422, 1961. The results of these analyses are shown in Table I, and clearly indicate that purification by silicic acid column effectively removes most of the pigments, unsaponifiables and non-urea-adduct-forming esters which are present in the commercially refined, bleached and deodorized soybean oil.

As can also be seen from the data in Table I, slightly better results are obtained when the soybean oil is passed through the column in the form of a hexane solution thereof, although even by using the oil alone on a dry column, the purified oil is considerably purer than either the starting oil (which is a commercially refined, bleached, and deodorized product) or a soybean oil isolated from a commercial oil in water emulsion.

TABLE I

ANALYSIS OF SOYBEAN OIL BEFORE AND AFTER PASSING THROUGH A SILICIC ACID COLUMN

| Oil Sample | Original Soybean Oil | Soybean Oil Purified with Dry Silicic Acid Column | Soybean Oil in Hexane Solution Purified with Silicic Acid Column | Oil Isolated from Intralipid* |
|---|---|---|---|---|
| Photometric Index 440 mµ Color | 11.4 | 6.0 | 3.6 | 37.7 |
| Photometric Index 550 mµ | 0.9 | 0.3 | 0.2 | 5.4 |
| Non-Urea-Adduct-Forming Ester (%) | 1.34 | 0.35 | 0.33 | 1.26 |
| Unsaponifiable Matter (%) | 0.50 | 0.15 | 0.12 | 0.63 |

*A commercially available soybean oil in water emulsion product.

The effectiveness of the silicic acid column in purifying the soybean oil can also be shown by thin layer chromatographic analysis according to the method described by W. S. Singleton, et al in Jour. Amer. Oil. Chem. Soc. 43, 592–595, 1966. Using this technique, a sample of the original soybean oil (D), as well as samples of the first 25 gm. of eluate (E) and the purified oil (F) were analyzed on silicic acid plates. FIG. 1 is a photograph of the thin layer chromatogram. As can be seen in FIG. 1, sample (D) contains considerable amounts of slow moving impurities near the starting line. These impurities correspond to the dark color band on the silicic acid column. Sample (E) contains only traces of these slower moving impurities, while sample (F) contains almost none of these impurities.

It should be noted that although in the foregoing example reference was made to hexane as a suitable solvent for the nutritive oil, other alkane solvents may also be employed. Thus, in general, suitable alkane solvents are those containing from 5 to 18 carbon atoms, a preferred class of alkanes being those containing from 5 to 10 carbon atoms. Mixtures of such alkanes may also be employed, e.g., petroleum ether. Of course, if alkane solvents are used that are gaseous at ambient temperatures, then they sould be kept under pressure so as to be in liquid form.

Where a solution of nutritive oil in an alkane solvent is utilized, rather than the oil alone, the ratio by volume of solvent to oil is generally from about 10:1 to 0.1:1, a more preferrable range being 4:1 to 0.2:1.

2. Sunflower oil

Figure 2:
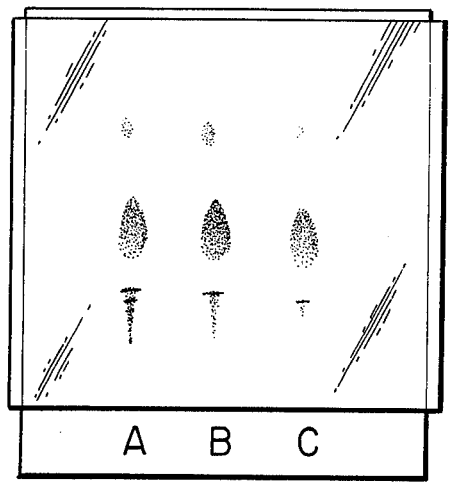
FIG. 2 is a photograph of a silicic acid thin layer chromatogram of a sunflower oil sample before and after purification on a silicic acid column.

The same experiments as described above were conducted with sunflower oil, and similar results were obtained as shown in Table II and FIG. 2.

TABLE II

ANALYSIS OF SUNFLOWER OIL BEFORE AND AFTER PASSING THROUGH A SILICIC ACID COLUMN

| Oil Sample | Fresh Sunflower Oil | Sunflower Oil Purified with Dry Silicic Acid Column | Sunflower Oil in Hexane Solution Purified with Silicic Acid Column |
|---|---|---|---|
| Photometric Index 440 mµ Color | 8.1 | 1.5 | 3.0 |
| Photometric Index 550 mµ | 0.9 | 0.1 | 0.2 |
| Non-Urea-Adduct-Forming Ester (%) | 1.71 | 0.21 | 0.29 |
| Unsaponifiable Matter (%) | 0.55 | 0.22 | 0.34 |

As can be seen from the data in Table II, the purification of sunflower oil by silicic acid column chromatograph effectively removes most of the impurities present in the starting oil.

FIG. 2 is a photograph of a thin layer silicic acid chromatogram of a sample of the original sunflower oil (A), a sample of the first 25 gm. of eluate (B), and a sample of the purified oil (C). As can be seen in FIG. 2, sample (A) contains considerable amounts of slow moving impurities which are not present to any appreciable extent in sample (C). Sample (B) contains minor amounts of these impurities.

Figure 3:
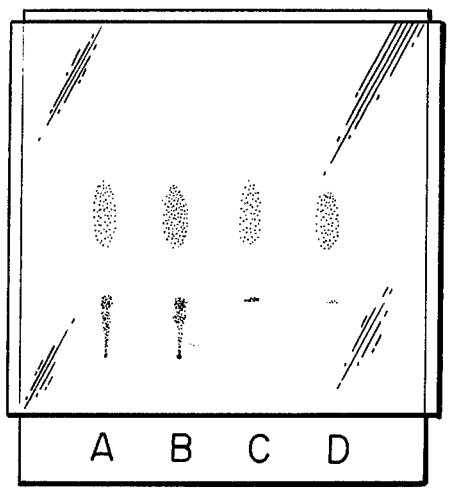
FIG. 3 is a photograph of a silicic acid thin layer chromatogram comparing individual samples of sunflower oil, namely: original sunflower oil (A), a soybean oil isolated from a commercially available product (B), sunflower oil which has been purified by passage through a silicic acid column (C), and soybean oil which has been purified by passage through a silicic acid column (D)

In addition, reference should be had to FIG. 3. FIG. 3 is a photograph of a silicic acid thin layer chromatogram comparing (A) a sample of the original sunflower oil;
(B) a sample of soybean oil isolated from Intralipid, a commercial oil in water emulsion made from soybean oil;
(C) a sample of purified sunflower oil; and
(D) a sample of purified soybean oil.

The oil (B), isolated from Intralipid, showed a significantly darker color and higher content of unsaponifiables and non-urea-adduct-forming esters than either the soybean oil or sunflower oil purified by the silicic acid column, and also had more and denser spots due to impurities than either of the purified oils.

II. PURIFICATION OF OILS BY SILICIC ACID FILTERING PAD

1. Sunflower oil

In addition to the silicic acid column chromatographic technique described above, the present invention can also be performed using a pad of silicic acid.

Thus, the treatment of the oil can be conveniently accomplished by filtering the oil through a ½ in. thick layer of silicic acid. When sunflower oil was filtered through a Buchner funnel prepacked with a ½ in. thick layer of silicic acid, the filtrate had the same color as the oil purified by passage through a column of silicic acid. To insure complete purification of the oil using this technique, the treatment can also be accomplished by filtering the oil several times through the silicic acid pad. When this is done, it is preferred that a fresh pad of silicic acid be used for the last filtration. (It should be noted that the foregoing technique may also be performed using a solution of the nutritive oil in a suitable solvent such as those described at page 8, second paragraph.)

Although the foregoing description referred to a one-half inch thickness for the silicic acid layer, it will, of course, be apparent that this particular thickness is not critical. Thus, the thickness may be from about ⅛ to was the sunflower oil purified by passage through a silicic acid column (E).

III. EVALUATION OF OTHER ADSORBENTS

Several other adsorbents were tested to ascertain their efficacy in the purification of sunflower oil. The procedure followed was essentially the same as that described above in II, with no solvent used. The oil used was a refined, bleached and deodorized sunflower oil. The adsorbents tested were silicic acid, silicic acid with 4% water, clay, silica gel, Florisil, Alumina and active carbon. The data in Table IV clearly demonstrate that silicic acid and silica gel are most suitable for the purification of oil for parenteral feeding, both from the standpoint of effectiveness in removing impurities and capacity for amount of oil. Alumina is particularly unsuitable because it may induce additional oxidation, decomposition and polymerization of the oil during the purification process.

TABLE IV
EVALUATION OF VARIOUS ADSORBENTS FOR PURIFICATION OF SUNFLOWER OIL

| Adsorbent | Capacity g.oil/300 g. adsorbent | Photometric Index 440 mμ | Photometric Index 550 mμ | Thin Layer Chromatographic Analysis | Non-urea-Adduct-Forming Esters |
|---|---|---|---|---|---|
| Silicic Acid[1] | 1500 | 1.5 | 0.0 | Good | 0.21 |
| Silicic Acid + 4% Water | 1500 | 1.2 | 0.0 | Excellent | 0.32 |
| Silicic Acid + 33% Clay[2] | 1000 | 1.7 | 0.0 | Excellent | 0.38 |
| Clay | 150 | 1.7 | 0.0 | Poor | — |
| Silica Gel[3] | 1500 | 1.8 | 0.0 | Excellent | — |
| Silica Gel[3A] | 836 | 2.0 | 0.0 | — | — |
| Florisil[4] | 520 | 1.8 | 0.0 | Fair | — |
| Alumina[5] | 200 | 4.0 | 0.0 | Fair | — |
| Alumina (reactivated) | 200 | 2.6 | 0.0 | Fair | — |
| Active Carbon[6] | 150 | 2.5 | 0.0 | Poor | — |

[1]Silicic Acid, Analytical Reagent, 100 mesh, #2847, Mallinckrodt Chemical Works.
[2]Tonsil, 60–90 mesh, Sud Chemie, A. G.
[3]Silica Gel, 0.05–0.2 mm., 70–325 mesh ASTM, EM Reagent, EM Lab., Inc.
[3A]Silica Gel, 30–70 mesh, Em Reagent, EM Lab., Inc.
[4]60–100 mesh, Fisher Scientific.
[5]80–200 mesh, Fisher Scientific.
[6]35–100 mesh, Norit, N.V. Fabriek.

4 inches, and preferably is from about ¼ to 2 inches.

Table III gives the results of photometric analyses of sunflower oil purified by filtration through a pad of silicic acid. For comparison purposes, the data for the original sunflower oil as well as for sunflower oil purified by passage through a silicic column are given.

TABLE III
PURIFICATION OF SUNFLOWER OIL BY FILTRATION THROUGH A LAYER OF SILICIC ACID

| | | Photometric Color 440 mμ | Photometric Color 550 mμ |
|---|---|---|---|
| (A) | Original Sunflower Oil | 4.8 | 0.8 |
| (B) | Oil Filtered Once through a ½" Layer of Silicic Acid | 1.5 | 0.0 |
| (C) | Oil Filtered 3 Times through a ½"0 Layer of Silicic Acid | 1.5 | 00 |
| (D) | Oil Filtered 3 Times through a ½" Layer of Silicic Acid then through a Fresh Layer of Silicic Acid | 1.5 | 0.0 |
| (E) | Oil Purified by Dry Silicic Acid Column | 1.5 | 0.0 |

Figure 4:
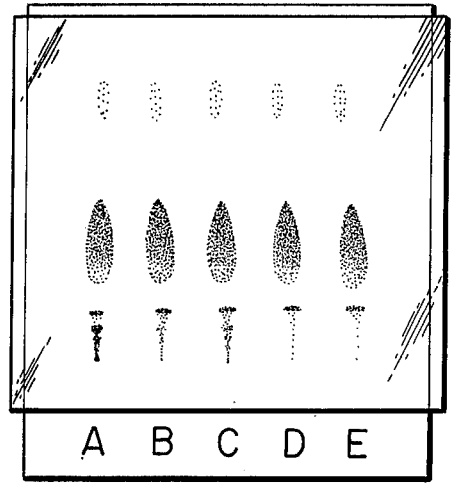
FIG. 4 is a photograph of a silicic acid thin layer chromatogram comparing individual samples of sunflower oil, namely: original sunflower oil (A), sunflower oil purified by passage through a filtering pad of silicic acid (B,C,D), and sunflower oil purified by passage through a silicic acid column (E).

Samples of each of these oils were analyzed by thin layer chromatography. FIG. 4 is a photograph of the thin layer chromatogram. As can be seen therein, sunflower oil filtered through silicic acid, particularly the oil which was filtered three times through a ½ in. layer of silicic acid and then once through a fresh ½ in. layer of silicic acid (D) was practically as free of impurities as

IV. PREVENTION OF AUTOXIDATION OF THE PURIFIED OILS

The soybean oil purified according to the process described above, i.e., by passing same through a silicic acid column was found to have a lower peroxide value than the original, unpurified oil, indicating that a substantial portion of the peroxides in the original oil was effectively removed by the silicic acid column. The pertinent data are given in Table V. However, the purified oil autoxidized faster than did the original oil during storage, as shown by the rate of increase in the peroxide value during storage of the oil at 60° C. Although the explanation for this is not known with absolute certainty, it is believed that the more rapid autoxidation of the purified oil is perhaps due to the removal of natural antioxidants, tocopherols, from the oil by the column, or that it is due to contamination of the oil by trace metals, such as iron, from the silicic acid used in the column.

I have found that the purified oil can be prevented from undergoing autoxidation by adding a tocopherol antioxidant, preferably γ-tocopherol, together with a metal scavenging agent such as ascorbyl palmitate. The additives should be added to the purified oil as soon as it is eluted from the silicic acid column.

As will be seen from a consideration of the data hereinafter, the use of (1) γ-tocopherol as an antioxidant additive for the purified nutritive oil, together with (2) a metal scavenging agent such as ascorbyl palmitate, dramatically enhances the oil's resistance to autoxidation.

The amount of γ-tocopherol which is added to the purified oil is generally from about 0.002 to 0.200 weight percent, based on the oil, with a range of 0.002 to 0.100 percent being preferred, and a range of from about 0.005 to 0.05 weight percent being most preferred.

The metal scavenging agent, e.g., ascorbyl palmitate, citric acid, or the like, is employed in conjunction with the tocopherol. The amount of said scavenging agent employed is limited by its solubility in the oil. For citric acid, the amount employed typically is about 0.01 weight per cent based on the oil. For ascorbyl palmitate, about 30 mg per 100 g of oil is the limit of its solubility. In general, it is preferred that the scavenging agent employed be present in an amount of at least about 0.01 weight percent, based on the oil.

While ascorbyl palmitate is a preferred metal scavenging agent, as previously noted, other metal scavengers may also be utilized, e.g., citric acid, Rosemary Extract, BHT (butylated hydroxytoluene), BHA (butylated hydroxyanisole), and the like.

As shown in Table V, 0.02% of γ-tocopherol and 30 mg/100 g. of ascorbyl palmitate, when added to the purified oil, can quite effectively stabilize the purified oil and prevent autoxidation thereof. In fact, the purified oil having these additives showed an even better stability than the original untreated soybean oil.

TABLE V

PREVENTION OF AUTOXIDATION OF PURIFIED SOYBEAN OIL WITH ANTIOXIDANTS

| | Peroxide Number* After Aging at 60° C for Days | | |
|---|---|---|---|
| | 0 | 3 | 6 |
| Original Oil | 0.12 | 0.75 | 3.39 |
| Oil Purified with Silicic Acid Column | 0.06 | 5.45 | 9.98 |
| Purified Oil + 0.02% α-tocopherol | — | 4.14 | 8.45 |
| Purified Oil + 0.02% γ-tocopherol | — | 2.73 | 6.19 |
| Purified Oil + 0.2% γ-tocopherol + 30 mg./100 g. ascorbyl palmitate | — | 0.13 | 0.21 |

*Official Method Cd-8-53; American Oil Chemist's Society

As shown in Table V, the original unpurified soybean oil undergoes a considerable degree of autoxidation within six days as evidenced by an almost 30 fold increase in peroxide number. However, the oil which has been purified by passage through a silicic acid column undergoes an even greater degree of autoxidation. Thus, while the purified oil has only half the peroxide content of the original, unpurified oil, it rapidly autoxidizes, so that after six days, there has been an almost 170 fold increase in peroxide number. The addition of 0.02% of either α- or γ-tocopherol alone, while slightly reducing the degree of autoxidation, is essentially ineffective in preventing autoxidation of the purified oil. However, when in addition to 0.02% of γ-tocopherol, there is also added 30 mg./100 g. of oil of ascorbyl palmitate, the autoxidation of the purified oil is significantly retarded.

Similar results were obtained with sunflower oil as shown in Table VI. The purified sunflower oil with both γ-tocopherol and ascorbyl palmitate as antioxidants was more stable than the original unpurified sunflower oil.

TABLE VI

PREVENTION OF AUTOXIATION OF PURIFIED SUNFLOWER OIL WITH ANTIOXIDANTS

| | Peroxide Number* After Aging at 60° C for Days | | |
|---|---|---|---|
| | 0 | 3 | 6 |
| Original Oil | 0.32 | 1.21 | 4.77 |
| Oil Purified with Silicic Acid Column | 0.05 | 3.89 | 10.31 |
| Purified Oil + 0.02% α-tocopherol | — | 3.19 | 9.04 |
| Purified Oil + 0.02% γ-tocopherol | — | 3.44 | 9.82 |
| Purified Oil + 0.02% γ-tocopherol + 30 mg./100 g. Ascorbyl Palmitate | — | 0.39 | 2.19 |

*Official Method Cd-8-53; American Oil Chemist's Society

The treatment of nutritive oils to remove the impurities described above is a very important factor as regards the suitability of such oils for intravenous feeding. Thus, the oils purified in accordance with the invention can be used to produce emulsions with fewer adverse physiological effects when used for intravenous feeding. The unsaponifiable matter which is removed from the oil by the process of the invention contains plant sterols, and it has been recently found that excessive amounts of plant sterols in an oil in water emulsion can cause adverse physiological effects when the emulsion is used for intravenous feeding. Moreover, the non-urea-adduct-forming esters which are also removed from the oils by the invention contain oxidative and thermal decomposition products, cyclic and polar monomers and oxidative and thermal polymers. The amount of such esters in commercial edible oils, such as soybean or sunflower oil, is usually about 1-2%. These undesirable compounds may be originally present in the oilseeds, but it is more likely that they are produced during the processing of the oil, including extraction, refining, bleaching and deodorization. Furthermore, even when the processing conditions are quite mild, such as those described in U.S. Pat. No. 3,169,094 and Swedish Pat. No. 220,400, the oil isolated from a commercial sample of an oil in water emulsion manufactured according to these patents, Intralipid, contained 1.26% of non-urea-adduct-forming esters. This is considerably higher than the non-urea-adduct-forming esters found in the oil purified according to this invention. Treatment of an oil by heat or by heat and oxygen will increase its content of non-urea-adduct-forming esters even more.

The toxic effects resulting from the ingestion of these non-urea-adduct-forming esters has been well documented. The symptoms include irritation of the digestive tract, organ enlargement (particularly enlargement of the liver), growth depression and in some cases, death. These effects are summarized in a review by Artman, "Advance in Lipid Research", Vol. 7, 245–330, 1960; while Firestone et al specifically reported the toxicity of non-urea-adduct-forming esters to rats, Jour. Amer. Oil Chem. Soc. 38, 253–257, 1961. Thus, the process of the invention, according to which oils with non-urea-adduct-forming esters essentially removed, represents a significant advance in the art since it enables one to produce oil in water emulsions with fewer adverse physiological effects when they are used for intravenous feeding.

There will now be given some preparative examples illustrating the preferred embodiments of the invention.

These examples are merely for illustrative purposes and are not to be considered as a limitation upon the scope of the invention which is hereinafter claimed.

PURIFICATION OF SOYBEAN OIL WITH SILICIC ACID

EXAMPLE 1

300 g. of washed and activated 100 mesh Analytical Reagent grade silicic acid were used to pack a glass chromatographic column of 40 mm. in diameter. The column was equipped with a coarse sintered glass disc at the bottom. A commercially refined, bleached, and deodorized soybean oil was passed through the column by applying a pressure of 10 psi to the top of the column. A vacuum created by a water aspirator was applied to the bottom of the column. The first 25 g. of the eluate which passed through the column was discarded. The passage of the soybean oil through the column was continued until the visible dark band in the column moved to a position near the bottom of the column. At this time, approximately 1,500 g. of eluate were collected as purified soybean oil.

EXAMPLE 2

The same procedure as described in Example 1 was conducted with the use of a commercially refined, bleached, and deodorized sunflower oil.

EXAMPLE 3

A glass chromatographic column 4 cm. in diameter and 60 cm. in length, with a coarse sintered glass disc at the bottom was closed at the end with a 4 mm. bore stopcock. Hexane was poured into the column to 10 cm. in height. 300 g. of washed and activated 100 mesh Analytical Reagent grade silicic acid were made into a slurry with hexane and then poured into the column. The stopcock was adjusted so that a 2-3 cm. layer of hexane remained on the top of the silicic acid column. A commercially refined, bleached, and deodorized soybean oil was mixed with hexane at a volume ratio of 1:1. The hexane solution of the oil was then poured into the column. A slight pressure was applied on top of the column to increase the flow rate. The first 50 ml. of eluate was discarded. The passing of the hexane solution of soybean oil through the column was continued until the colored band moved close to the bottom of the column. Approximately 10,000 ml. of the hexane solution were collected up until this point as eluate. The hexane was then removed from the solution under vacuum at 60° C. If necessary, the last traces of solvent may be removed by vacuum steam distillation at temperatures below 60° C. Approximately 1500 g. of purified soybean oil were thus obtained.

PURIFICATION OF SUNFLOWER OIL ON A SILICIC ACID FILTRATION PAD

EXAMPLE 4

A Buchner funnel of 600 ml. capacity with a 90 mm. diameter coarse fritted disc sealed in at the bottom was connected to a filtering flask. The flask was evacuated by using a water aspirator. Washed and activated 100 mesh Analytical Reagent silicic acid was poured into the funnel and packed as a tight uniform layer on the bottom of the funnel to a depth of 0.5 inch. 500 g. of a commercially refined, bleached, and deodorized sunflower oil were filtered through the funnel to obtain purified oil. The filtration was repeated twice more through the silicic acid layer, and finally once more through a fresh layer of silicic acid, whereby a purified sunflower oil was obtained.

STABILIZATION OF PURIFIED SOYBEAN AND SUNFLOWER OILS

EXAMPLE 5

Samples of each of the purified oils produced in Examples 1-4 were, immediately after being obtained, subjected to stabilization to prevent autoxidation thereof. To each sample there were added 0.02% of γ-tocopherol and 30 mg./100 gm. of oil of ascorbyl palmitate.

PREPARATION OF OIL IN WATER EMULSIONS WITH TREATED SUNFLOWER OIL

EXAMPLE 6

50 g. of sunflower oil which had been purified with a silicic acid column and to which had been added 0.02% γ-tocopherol and 30 mg./100 g. ascorbyl palmitate, were mixed with 6.0 g. of an active carbon bleached ethanol soluble fraction of egg phosphatides, 25 g. of glucose, and 450 g. of distilled, pyrogen-free water at approximately 80° C. until a coarse emulsion was obtained. The emulsion was then homogenized with the use of a Manton-Gaulin homogenizer at 5,000 psi at 50°-60° C. to obtain the desired emulsion. The product was autoclaved in a known manner to destroy possibly occurring bacteria and spores. An oil in water emulsion suitable for parenteral feeding with no adverse physiological effects was thereby obtained.

Referring to Example 6, it is important to note that sunflower oil is superior to other nutritive oils because sunflower oil is easy to refine to a light colored product containing fewer undesirable impurities than other nutritive oils. It exhibits reasonably good stability against thermal and oxidation decomposition, since it contains very little linolenic acid. Moreover, it contains a relatively high content of nutritious linoleic acid.

PREPARATION OF 10% OIL IN WATER EMULSION WITH SOYBEAN OIL AND EGG PHOSPHATIDES

EXAMPLE 7

Twelve grams of the ethanol-soluble fraction of phosphatides from egg yolk are dissolved in 200 ml. of water. The phosphatide solution is placed in a separatory funnel and is added, drop-by-drop, to a 1500 ml. beaker containing 100 grams of soybean oil, prepared according to the method described in Example 1, with constant stirring, using a magnetic stirring bar. Further, 100 ml. of water is then added to the oil via the separatory funnel. Next, a solution 22 grams of glycerol dissolved in 40 ml. of water is added to the oil/water solution. Sufficient water to make 1 Kg. of emulsion is added to the oil at a faster rate, while the mixture is constantly stirred. The crude emulsion thus prepared is warmed to 50° C with stirring, and is poured into the feeder tank of the Gaulin homogenizer (15M). The homogenizer is turned on, applying pressure gradually to the second stage to 800 psig, followed by applying pressure gradually to the first stage to a total pressure of 5000 psig. The emulsion is passed through the homogenizer 10-15 times. The temperature of the emulsion is maintained between 50°-60° C. by partially immersing the beaker containing the emulsion in cold water. The emulsion thus prepared is collected in screw-capped bottles.

Analysis of the emulsion is shown in Table VII. The particle size was analyzed by a Coulter Counter.

TABLE VII

ANALYSIS OF SOYBEAN OIL EMULSION MADE WITH EGG PHOSPHATIDES

| | pH | FFA (meq./liter) | Particle Size Distribution (% Vol. >$\mu$) | | |
|---|---|---|---|---|---|
| | | | 0.5 $\mu$ | 1.0 $\mu$ | 2.0 $\mu$ |
| Original | 8.14 | 0.72 | 74.0 | 17.0 | 1.0 |
| After Sterilization | 7.90 | 1.05 | 63.0 | 1.0 | 0.0 |
| Store at 60° C. | | | | | |
| 1 week | 6.40 | 2.10 | 63.0 | 1.0 | 0.0 |
| 2 weeks | 6.10 | 2.96 | 63.0 | 2.0 | 0.0 |
| 3 weeks | 6.07 | 3.20 | 63.0 | 2.0 | 0.0 |
| 4 weeks | 6.02 | 3.70 | 64.0 | 2.0 | 0.0 |
| Freezing and Thawing | | | | | |
| 1 cycle | 7.10 | | 74.0 | 36.0 | 20.0* |
| 2 cycles | 7.15 | | 84.0 | 43.0 | 25.0* |
| 3 cycles | 7.05 | | 84.0 | 42.0 | 6.0* |
| 4 cycles | 7.05 | | 84.0 | 40.0 | 20.0* |
| 5 cycles | 7.04 | | 85.0 | 38.0 | 20.0* |
| Shaking at Room Temp. | | | | | |
| 10 days | 7.42 | | 78.0 | 1.0 | 0.0 |
| 20 days | 7.38 | | 78.0 | 2.0 | 0.0 |
| 30 days | 7.39 | | 77.0 | 3.0 | 1.0 |

*No separation
FFA : meq. palmitic acid/liter emulsion

PREPARATION OF 10% OIL IN WATER EMULSION WITH SOYBEAN OIL AND SOYBEAN PHOSPHATIDES

EXAMPLE 8

The same procedure as used in Example 7 is used to produce an oil-in-water emulsion, except that the ethanol soluble fraction of soybean phosphatides was used to replace the egg phosphatides. The analytical data of the emulsion is shown in Table VIII.

TABLE VIII

ANALYSIS OF SOYBEAN OIL EMULSION MADE WITH EGG PHOSPHATIDES

| | pH | FFA (meq./liter) | Particle Size Distribution (% Vol. >$\mu$) | | |
|---|---|---|---|---|---|
| | | | 0.5 $\mu$ | 1.0 $\mu$ | 2.0 $\mu$ |
| Original | 7.15 | 0.79 | 56.0 | 10.0 | 1.5 |
| After Sterilization | 6.83 | 1.15 | 43.0 | 3.0 | 1.0 |
| Store at 60° C. | | | | | |
| 1 week | 6.10 | 3.2 | 44.0 | 5.0 | 1.0 |
| 2 weeks | 6.05 | 3.4 | 45.0 | 4.0 | 1.0 |
| 3 weeks | 6.04 | 3.6 | 44.0 | 4.0 | 1.0 |
| 4 weeks | 6.02 | 3.6 | 44.0 | 4.0 | 1.0 |
| Freezing and Thawing | | | | | |
| 1 cycle | 6.55 | | 46.0 | 2.0 | 0.0 |
| 2 cycles | 6.58 | | 54.0 | 2.0 | 0.0 |
| 3 cycles | 6.40 | | 61.0 | 2.5 | 0.0 |
| 4 cycles | 6.39 | | 58.0 | 2.0 | 0.0 |
| 5 cycles | 6.35 | | 56.0 | 1.0 | 0.0 |
| Shaking at Room Temp. | | | | | |
| 10 days | 6.67 | | 45.0 | 3.0 | 1.0 |
| 20 days | 6.66 | | 44.0 | 2.0 | 1.0 |
| 30 days | 6.43 | | 49.0 | 2.0 | 1.0 |

EXAMPLE 9

Same procedure as was used in Example 7 was used to produce an oil-in-water emulsion, except sunflower oil was used to replace soybean oil. The emulsion had similar properties as that of Example 7.

EXAMPLE 10

Same procedure as was used in Example 8 was used to produce an oil-in-water emulsion, except sunflower oil was used to replace soybean oil. The emulsion had similar properties as that of Example 8.

Although the purification method heretofore described in accordance with one aspect of my invention has made reference to such nutritive oils as sunflower oil and soybean oil, it is to be understood that my purification method is likewise applicable to other nutritive oils suitable for oil-in-water emulsions for use in parenteral administration. Examples of other suitable nutritive oils include cottonseed oil, corn oil, peanut oil, coconut oil, safflower oil, edible fats such as tallow and lard, and their fractionated products, etc.

The nutritive oil-in-water emulsions prepared in accordance with the present invention preferably contain the nutritive oil in an amount of from about 5 to 50 weight percent, based on the overall emulsion, a more preferred range being from 10 to 25 weight percent.

Variations and modifications can, of course, be made without departing from the spirit and scope of my invention.

Having thus described my invention, what I desire to obtain by Letters Patent and hereby claim is:

1. A nutritive oil-in-water emulsion suitable for parenteral administration, comprising an oil selected from the group consisting of soybean oil and sunflower oil, an emulsifier for said oil, and water wherein the improvement comprises:
    contacting said nutritive oil with an adsorbant selected from the group consisting of silicic acid and silica gel, to substantially remove non-urea-adduct forming esters and unsaponifiable matter from said nutritive oil, recovering said oil from the adsorbant, and subsequently combining the recovered nutritive oil with sterile water and an emulsifier to produce an improved oil-in-water emulsion.

2. A nutritive oil-in-water emulsion as described in claim 1, wherein said oil is mixed with a solvent at the time it is contacted with said adsorbant.

3. A nutritive oil-in-water emulsion as described in claim 1, wherein said emulsion includes a tocopherol and a metal scavenger to inhibit the autoxidation of the emulsified oil.

4. A nutritive oil-in-water emulsion as described in claim 3, wherein said oil recovered from said adsorbant is sunflower oil and contains no more than about 0.29% of non-urea-adduct-forming esters, and contains no more than about 0.34% unsaponifiable matter.

5. A nutritive oil-in-water emulsion as described in claim 3, wherein said oil recovered from said adsorbant is soybean oil and contains no more than about 0.35% of non-urea-adduct-forming esters, and contains no more than about 0.15% unsaponifiable matter.

6. A method of purifying a nutritive oil selected from the group consisting of soybean oil and sunflower oil to remove non-urea-adduct forming esters and unsaponifiable matter therefrom, said method comprising contacting said nutritive oil with an adsorbant selected from the group consisting of silicic acid and silica gel to substantially adsorb non-urea-adduct forming esters and unsaponifiable matter contained in said oil on the adsorbant and recovering the thusly purified oil from the adsorbant.

7. A method of purifying a nutritive oil as described in claim 6, wherein said oil is mixed with a solvent at the time it is contacted with said adsorbant.

* * * * *